(12) United States Patent
Kohlmann et al.

(10) Patent No.: US 11,740,181 B2
(45) Date of Patent: Aug. 29, 2023

(54) PREPARATION DEVICE, DIAGNOSTIC APPARATUS, DIAGNOSTIC KIT AND DIAGNOSTIC SYSTEM

(71) Applicant: BLOOM DIAGNOSTICS AG, Zürich (CH)

(72) Inventors: Angelica Kohlmann, Zürich (CH); Thomas Vincent Küpper, Zürich (CH)

(73) Assignee: BLOOM DIAGNOSTICS AG, Zurich (CH)

( * ) Notice: Subject to any disclaimer, the term of this patent is extended or adjusted under 35 U.S.C. 154(b) by 398 days.

(21) Appl. No.: 16/765,269

(22) PCT Filed: Dec. 13, 2018

(86) PCT No.: PCT/EP2018/084828
§ 371 (c)(1),
(2) Date: May 19, 2020

(87) PCT Pub. No.: WO2019/115725
PCT Pub. Date: Jun. 20, 2019

(65) Prior Publication Data
US 2020/0371031 A1    Nov. 26, 2020

(30) Foreign Application Priority Data

Dec. 13, 2017    (CH) .................................... 01514/17

(51) Int. Cl.
*G01N 21/64*    (2006.01)
*G01N 21/84*    (2006.01)
(Continued)

(52) U.S. Cl.
CPC ..... *G01N 21/6428* (2013.01); *G01N 21/8483* (2013.01); *G01N 33/54388* (2021.08);
(Continued)

(58) Field of Classification Search
CPC .......... G01N 21/6428; G01N 21/8483; G01N 33/74; G01N 2021/0118;
(Continued)

(56) References Cited

U.S. PATENT DOCUMENTS

| 2013/0224771 A1 | 8/2013 | McDade et al. |
| 2016/0169882 A1* | 6/2016 | Snider ................ G01N 33/5302 422/424 |

(Continued)

FOREIGN PATENT DOCUMENTS

| EP | 2 835 643 A1 | 2/2015 |
| WO | 2008075213 A2 | 6/2008 |

(Continued)

OTHER PUBLICATIONS

International Search Report dated May 20, 2019, in International Application No. PCT/EP2018/084828.

*Primary Examiner* — Mark R Gaworecki
(74) *Attorney, Agent, or Firm* — MEDLER FERRO WOODHOUSE & MILLS PLLC

(57) ABSTRACT

A preparation device for preparing a sample for measurement of a target biomolecule in a probe of a bodily fluid is disclosed that includes a substrate with a capillary network configured to transport the probe of the bodily fluid along the substrate. The substrate may be provided with a fluorescent, reflective or self-luminescent marker adapted to bind with the target biomolecule to emit a reaction radiation when excited by an excitation source. The fluorescent, reflective or self-luminescent marker is adapted, when bound to the target biomolecule and excited by the excitation source, together with the target biomolecule to emit the reaction radiation at an intensity proportional to a quantity of the target biomolecule in the probe of the bodily fluid.

13 Claims, 2 Drawing Sheets

(51) Int. Cl.
    *G01N 33/74*     (2006.01)
    *G01N 33/543*    (2006.01)
    *G01N 21/01*     (2006.01)

(52) U.S. Cl.
    CPC ..... *G01N 33/74* (2013.01); *G01N 2021/0118* (2013.01); *G01N 2021/6436* (2013.01); *G01N 2021/6439* (2013.01); *G01N 2021/8494* (2013.01); *G01N 2800/367* (2013.01)

(58) Field of Classification Search
    CPC ... G01N 2021/6436; G01N 2021/6439; G01N 2021/8494; G01N 2800/367
    See application file for complete search history.

(56) References Cited

U.S. PATENT DOCUMENTS

2016/0349185 A1* 12/2016 Park ................... G01N 21/8483
2017/0350821 A1* 12/2017 Delamarche ..... G01N 35/00069

FOREIGN PATENT DOCUMENTS

| WO | WO-2014089700 A1 * | 6/2014 | ............ G01J 3/0272 |
| WO | WO-2014147074 A1 * | 9/2014 | ............. G01N 21/75 |

* cited by examiner

PREPARATION DEVICE, DIAGNOSTIC APPARATUS, DIAGNOSTIC KIT AND DIAGNOSTIC SYSTEM

TECHNICAL FIELD

The present invention relates to a preparation device according to the preamble of independent claim 1 and more particularly to a diagnostic apparatus having such a preparation device as well as a diagnostic kit and a diagnostic system having such a diagnostic apparatus and such a preparation device.

Such preparation device comprising a substrate with a capillary network configured to transport a probe of a bodily fluid along the substrate, wherein the substrate is provided with a fluorescent, reflective or self-luminescent marker adapted to bind with a target biomolecule to emit a reaction radiation, eventually, when excited by an excitation source, can be used for the preparation of the sample for measuring the target biomolecule in the probe of the bodily fluid.

BACKGROUND ART

For determining the condition of human or animal beings in many cases it is desired to analyze bodily fluids. Typically, a probe of the bodily fluid of a patient is gathered by a doctor or another medically trained person and provided in an appropriate containment. The probe is then analyzed in a laboratory using suitable devices such as spectrometers, chemical reaction tests or the like. In this way, a marker typically being a biomolecule indicative for a specific situation such as a disease or an ability of the patient can be identified or measured.

For example, for testing fertility of women it is known to measure the quantity of Anti-Müllerian hormone (AMH) or Müllerian-inhibiting hormone (MIH) in the blood. From this measurement, the ovarian reserve can be determined allowing to conclude the condition of the patient with regard to fertility.

More specifically, in a known fertility testing procedure a doctor gathers a sample of blood from a female patient and provides the sample to a laboratory. There, the probe of blood is analyzed by measuring the level of AMH using a specific antibody which binds to AMH and allows for efficient detection. The doctor is then provided with the results from the laboratory which allow him to conclude about the patient's fertility condition and to establish suitable measures, if required.

However, even though in many instances such testing is accurate and reliable, it causes a comparably high effort and, therefore, is perceived as cumbersome. Furthermore, such testing usually is comparably costly. These aspects may result in that the testing is not regularly and/or not early enough performed to allow a widespread early stage identification of the specific condition. However, for many indications the quality of treatment can be increased by early identification and by getting a better statistical overview about the specific indication in the population or a group thereof.

Therefore, there is a need for a system allowing an efficient testing and/or evaluation of a patient with regard to a specific indication such as fertility.

DISCLOSURE OF THE INVENTION

According to the invention this need is settled by a preparation device as it is defined by the features of independent claim 1, by a diagnostic apparatus as it is defined by the features of independent claim 16, by a diagnostic kit as it is defined by the features of independent claim 30 and by a diagnostic system as it is defined by the features of independent claim 33. Preferred embodiments are subject of the dependent claims.

In particular, in one aspect the invention deals with a preparation device for preparing of a sample for measurement of a target biomolecule in a probe of a bodily fluid. The preparation device comprises a substrate with a capillary network configured to transport the probe of the bodily fluid along the substrate. The substrate is provided with a fluorescent, reflective or self-luminescent marker adapted to bind with the target biomolecule to emit a reaction radiation, eventually, when excited by an excitation source. The fluorescent, reflective or self-luminescent marker is adapted, when bound to the target biomolecule and excited by the excitation source or self-shining, together with the target biomolecule to emit the reaction radiation at an intensity proportional to a quantity of the target biomolecule in the probe of the bodily fluid. In particular, in case the marker is fluorescent or reflective, it can emit the reaction radiation when excited by the excitation source. In case it is a self luminescent marker, it can emit the reaction radiation without being excited, i.e. it is self luminescent.

The quantitative measurement can be achieved by measuring the concentration of the target biomolecule. In particular, the concentration allows for efficiently derive the quantity of the target biomolecule in the bodily fluid. Such measuring can be comparable or similar to complex laboratory assays but embodied in a comparably simple and efficient manner. Specifically, the concentration or the target biomolecule can be determined by reference to a standard curve consisting of known concentrations of a purified reference biomolecule.

The bodily fluid can be any bodily fluid like urine, lymph, saliva, swat or the like and particularly blood. The target biomolecule can be a protein or peptide such as a hormone. It preferably is an anti-mullerian hormone (AMH) indicative of an ovarian reserve of an individual to whom the bodily fluid sample belongs.

In the context of the invention, the term "biomolecule" or biological material can relate to a molecule present in a human or animal organism. Biomolecules may comprise large molecules such as proteins, carbohydrates, lipids, and nucleic acids, as well as small molecules such as primary metabolites, secondary metabolites, and natural products. For example, pharmaceutical drugs as biomolecules may be natural products or semisynthetic or they may be totally synthetic.

The fluorescent, reflective or self-luminescent marker can be an antibody. For being reflective it can comprise gold or the like. In particular, the fluorescent, reflective or self-luminescent marker preferably comprises an anti-mullerian hormone antibody in a known concentration. Such an antibody can be immobilized on the substrate or strip in a known concentration.

The substrate can also be provided with a plurality of fluorescent, reflective or self-luminescent markers adapted to bind with other target biomolecules to emit a reaction radiation when excited by an excitation source. Like this, a combined analysis, e.g. with respect to several indications, can efficiently be provided. In such embodiments, the different fluorescent, reflective or self-luminescent markers preferably are adapted such that they emit a reaction radiation having an easily distinguishing radiation spectrum and, particularly, different spectral peaks.

The substrate can be embodied for example as a test strip. For equipping the substrate with the fluorescent, reflective or self-luminescent marker known techniques such as spraying or the like can be used.

The excitation can be light, bio/chemical luminescence or the like. Thus, the excitation source can be a light source. The reaction radiation can particularly be a light spectrum or an electromagnetic spectral profile emitted by a complex comprising of the target biomolecule and the fluorescent, reflective or self-luminescent marker.

By using the preparation device according to the invention, it is possible to measure the reaction radiation or its intensity to determine the quantity of the target biomolecule in the bodily fluid. In particular, by providing the appropriate fluorescent, reflective or self-luminescent marker, the preparation device allows for identifying and, in addition, to quantifying the target biomolecule in the sample. In some instances it may be necessary to, e.g. electronically, correcting the intensity of the reaction radiation in order to eliminate or reduce background noise contained in the measured intensity. In many applications such as in fertility testing, this quantification is highly important and a pure identification is not sufficient. Thus, the preparation device allows for an efficient testing of a patient with regard to a specific indication represented by the amount of the target biomolecule in the bodily fluid. In particular, the patient can apply self-testing and does not require a doctor or other medically educated person for the testing per se. This allows to decrease the effort involved in testing such that acceptance can be increased and regular testing can be achieved.

Preferably, the preparation device comprises a case housing the substrate, wherein the case is adapted to cooperate with a diagnostic apparatus having the excitation source, for the measurement of a quantity of the target biomolecule in the probe of the bodily fluid, based on the intensity of the emitted reaction radiation. Such a case allows for protecting the substrate such that impairments to the substrate can be minimized or prevented. Also, such case allows for a comparably convenient handling of the preparation device particularly in connection with the diagnostic apparatus.

Thereby, the case preferably has a window for indicating when a predefined quantity of the probe of the bodily fluid is collected. For example, the predefined quantity sample can be in a range of about 2 microliter ($\mu l$) to about 100 $\mu l$ or in arrange of about 10 $\mu l$ to about 50 $\mu l$ or it can be about 20 $\mu l$ of bodily fluid such as blood. Such a window allows for easily controlling or assuring that an appropriate amount of the probe is provided to the preparation device. In particular, when the bodily fluid is conveniently visible on the substrate such a window can be a very efficient implementation of control of the amount.

Preferably, the fluorescent, reflective or self-luminescent marker comprises a protein displaying an intrinsic fluorescence. Such a protein allows for efficiently quantifying the target biomolecule on the substrate and, thus, in the bodily fluid.

The preparation device can be equipped with a test line which contains an additional marker such as additional antibodies specific to the target biomolecule. Once the sample reaches the test line an optical change such as the line optically appearing can occur allowing the test to be identified as concluded or as positive. By providing the additional marker it can be achieved that the control line only appears when the target biomolecule is present. Such test line allows for ensuring that an appropriate amount of the sample is provided to the substrate.

The preparation device preferably comprising a calibration marker to validate the correct functioning of the preparation device by checking on a relationship between values measured by means of the preparation device and corresponding known values derived from a standard function. Such calibration allows to increase the quality of the overall measurement. Thereby, the calibration marker preferably comprises a protein, such as a $\alpha$-fetoprotein (AFP) or Vitamin D allowing for an efficient and specific calibration of the target biomolecule. The calibration marker preferably is arranged in a line on the reaction area. Also the fluorescent, reflective or self-luminescent marker preferably is arranged in a line on the reaction area.

Preferably, the fluorescent, reflective or self-luminescent marker is arranged such that, when bound to the target biomolecule and excited by the excitation source, the intensity of the emitted reaction radiation is measurable in a spectral emission curve. Such measurement allows for a quick and accurate determination of the quality of the target biomolecule in the sample.

Thereby, the power spectrum of the radiation emission preferably comprises a peak corresponding to the quantity of the target biomolecule in the probe of the bodily fluid. The power spectrum of the radiation emission can be displayed or depicted as power spectral intensity of an emission curve. Such peak allows for a sufficient precise determination of the quantity of the target biomolecule by approximation. In particular, when there is one single peak, the spectrum is comparably narrow and/or the peak is comparably high such approximation may be appropriately accurate.

Preferably, the preparation device comprises a wireless communication arrangement, such as a near field communication arrangement, storing a unique identifier of the preparation device. Generally, the acronym NFC relates to near field communication being a set of communication protocols that enable two or more electronic devices to establish communication by bringing them close to each other such as, e.g. within 4 cm of each other. Such a NFC arrangement allows for efficient communication or data provision to another device such as to a diagnostic apparatus or the like. Thereby, the near field communication arrangement preferably is integral with the case. Such embodiment allows for a robust and efficient setup of the NFC.

The near field communication arrangement preferably is writable and adapted to keep record of usage of the preparation device. Like this, the history of the preparation device can be documented which allows for involving the circumstances in evaluation. Thereby, the NFC arrangement preferably is adapted to store a quantity value of the target biomolecule in the probe of the bodily fluid measured by a diagnostic apparatus and/or a unique identifier of the diagnostic apparatus.

In particular, the NFC arrangement preferably is adapted to store calibration information, information for identification of the biological ingredients used in the preparation device and information for traceability of the biological ingredients used in the preparation device. Also, such information may increase the quality of the evaluation or measurement.

Another aspect of the invention relates to a diagnostic apparatus for the measurement of a quantity of target biomolecule in a probe of a bodily fluid prepared by a preparation device as described above. The diagnostic apparatus comprises: (i) a seat arranged to accommodate the preparation device in a predefined position and orientation; (ii) an excitation source adapted to illuminate a substrate of the preparation device; (iii) an optical assembly adapted to measure power spectral intensity values of a reaction radiation emitted by a product of reaction on the preparation device, wherein the power spectral intensity values are proportional to a quantity of the target biomolecule in the probe of the bodily fluid; and (iv) an electronic assembly adapted to process and convert the power spectral intensity values measured by the optical assembly to a quantity value of the target biomolecule in the probe of the bodily fluid. The electronic assembly comprises a data exchange equipment adapted to receive data from the preparation device and to send data to a remote handheld communication device adapted to receive and display the quantity value of the target biomolecule in the probe of the bodily fluid.

The term "handheld communication device" can relate to any suitable portable computing device having a communication interface such as a smartphone, a tablet computer or a laptop computer.

The data exchange equipment can for example be provided to transfer, i.e. sending and receiving, data stored on an NFC tag on the preparation device via Bluetooth or a similar communication system. It can comprise a second or further NFC tag for automated pairing of the Bluetooth or similar communication system.

For determining the quantity of the target biomolecule in the probe of the bodily fluid by means of the preparation device, the diagnostic apparatus can efficiently be used as lateral flow reader to provide a fully quantitative assay result. By utilizing unique wavelengths of light for illumination, e.g., in conjunction with either complementary metal-oxide-semiconductor (CMOS) or charge-coupled device (CCD) detection technology, a signal rich image can be produced of the actual test line. Using image processing algorithms specifically designed for a particular test type and medium, line intensities can then be correlated with target molecule concentrations.

The diagnostic apparatus according to the invention allows for implementing the effects and benefits described above in connection with the preparation device and its preferred embodiments. In particular, it can be comparably simple in construction and handling such that it can be operated by an unskilled user like the patient himself.

Preferably, the diagnostic apparatus comprises a database storage adapted to store quantity values of the target biomolecule in the probe of the bodily fluid. Such database storage allows for tracking a sequence of measurements of the target biomolecule or the indication related thereto. In particular, when a specific course of the indication is to be observed such data storing can be particularly beneficial.

In a preferred embodiment of the diagnostic apparatus the data exchange equipment comprises a NFC structure adapted to store a unique identifier of the diagnostic apparatus and adapted to exchange data with a near field communication NFC arrangement of the preparation device. Such NFC structure and arrangement allows communication between the diagnostic apparatus and the associated preparation device.

Preferably, the diagnostic apparatus comprises a housing including the seat. Such housing allows for protecting the sensitive parts of the apparatus and for an efficient handling. The seat allows for accommodating a preparation device for evaluation. Like this, the position and orientation of the preparation can precisely be established in a convenient manner.

In particular, when the preparation device is arranged in the seat or the housing, the optical assembly preferably is arranged to ensure a first measurement alignment between the excitation source and the substrate of the preparation device illuminated thereby and to ensure a second measurement alignment between the substrate of the preparation device emitting the reaction light and the electronic assembly.

The housing of the apparatus preferably comprises a guide for sliding the preparation device relative to the housing into the predefined position and orientation. Such guide allows for convenient positioning of the preparation device on or in the diagnostic apparatus.

Preferably, the optical assembly is arranged to subtract illumination light by the excitation source from a light reflected by the preparation device such that the reaction light emitted by the product of reaction on the substrate of the preparation device is isolated. Thereby, the electronic assembly preferably comprises a photo sensor adapted to measure the reaction light emitted by the product of reaction on the substrate of the preparation device, once isolated from the illumination light by the excitation source. Such isolation can allow to achieve a comparably disturbance free accurate measuring.

The electronic assembly preferably comprises a digital processor programmed to execute algorithms on a signal corresponding to the measured quantity value of the target biomolecule in the probe of the bodily fluid. Such digital processor allows for an efficient evaluation of the signal. The diagnostic apparatus preferably comprises an analog-to-digital converter (ADC) cooperating with the photo sensor for digitalization of the measured quantity value of the target biomolecule in the probe of the bodily fluid.

Preferably, the electronic assembly comprises an energy storage device, such as a battery or accumulator and/or a connection to an external power supply, adapted to power electronic components of the diagnostic apparatus. Such energy storage device or connection allows for providing electric energy to the power consuming components of the diagnostic apparatus.

Preferably, the data exchange equipment of the electronic assembly is configured to identify the remote handheld communication device of an authorized user and to send data exclusively to the authorized remote handheld communication device. By having such authorization mechanism, it can be prevented that any data is transferred to an inappropriate person or device. Like this, safety of the diagnostic apparatus and particularly of its use can be essentially increased.

Thereby, the data exchange equipment of the electronic assembly preferably is configured to identify the remote handheld communication device by providing a unique pairing identification to the remote handheld communication device and by receiving a match signal from the remote handheld communication device. Such individualized pairing mechanism can be an efficient implementation of the authorized communication.

Another further aspect of the invention relates to a diagnostic kit comprising a preparation device as described above and a diagnostic apparatus as described above. Such a kit allows for efficiently equipping a patient with what he or she requires for an efficient self testing. In particular, it allows for implementing effects and benefits described above in connection with the preparation device and its preferred embodiments as well as with the diagnostic apparatus and its preferred embodiments.

Preferably, the diagnostic kit comprises a lancet. Such a lancet can be separate or integrated in the preparation device. It allows for efficiently drawing of blood or another bodily fluid of the patient and for providing it to the preparation device.

Preferably, the diagnostic kit comprises a computer program adapted to be stored and executed on a mobile communication device to establish communication with the diagnostic apparatus. Such a computer program allows for customizing the communication device such that it is able to be integrated or part of the testing system.

Still another further aspect of the invention relates to a diagnostic system comprising a preparation device as described above, a diagnostic apparatus as described above, a server and a mobile communication device adapted to communicate with the diagnostic apparatus and the server. The server is arranged to receive data signals from the mobile communication device corresponding to measured quantity values of a target biomolecule in probes of a bodily fluid and to send data signals to the mobile communication device corresponding to an evaluation of the measured quantity values.

Such diagnostic system allows for implementing effects and benefits described above in connection with the preparation device and its preferred embodiments as well as with the diagnostic apparatus and its preferred embodiments and the diagnostic kit and its preferred embodiment. In particular, with the diagnostic system data measured or obtained by the diagnostic apparatus via the preparation device can be evaluated and augmented. Like this, tools for drawing conclusions in order to enable a high-quality therapy can be provided. In particular, such system allows for a real-time evaluation and giving the practitioner a real-time feedback.

Preferably, the server comprises a data storage and is adapted to anonymize data received from the communication device, to store the anonymized data in the data storage, to evaluate the stored data with respect to a specific topic and provide results of the evaluation of the stored data. Such result provision, e.g., in form of statistics or graphs can help to achieve improved or better reasoned decisions regarding a specific therapy or application. For example, it can help to identify and present possibilities of fertility treatments or measures.

Providing the results of the evaluation of the stored data can be done by displaying the results in an advantageously protected section on a website. Or it can be a transfer to any computer connected to the server, e.g., via Internet. Preferably, providing the results of the evaluation of the stored data comprises sending data signals corresponding to the results of the evaluation of the stored data to the mobile communication device.

Preferably, evaluating the stored data with respect to a specific topic comprises generating a forecast of a medical outcome for a specific user. By using data gathered in previous testing for comparable patients, conclusions to a specific situation can be drawn. Such conclusions may help to improve the quality of treatment. In particular, the diagnostic system is arranged to be applied for pharmacovigilance or clinical trials.

BRIEF DESCRIPTION OF THE DRAWINGS

The preparation device according to the invention, the diagnostic apparatus according to the invention, the diagnostic system according to the invention and the diagnostic kit according to the invention are described in more detail herein below by way of an exemplary embodiment and with reference to the attached drawings, in which.

DESCRIPTION OF EMBODIMENTS

In the following description, certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
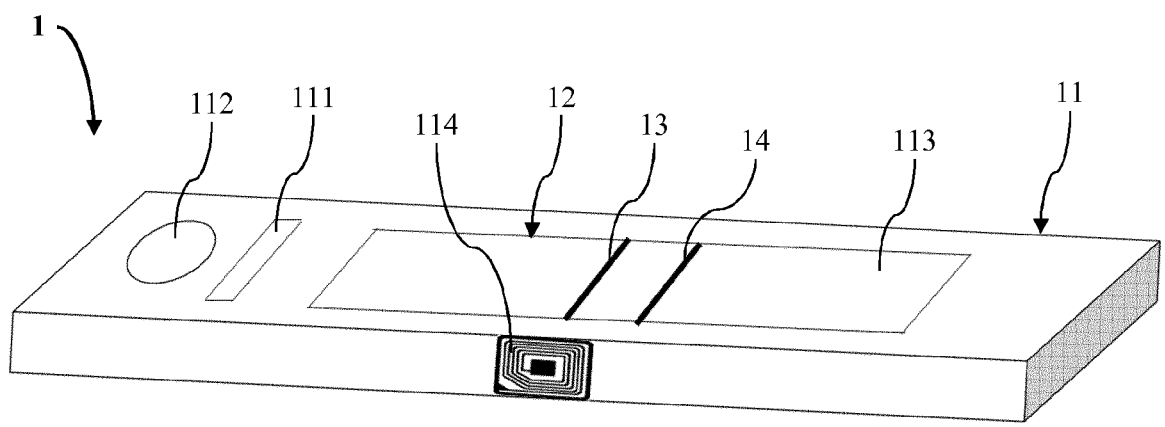
FIG. 1 shows a schematic perspective view of an embodiment of the preparation device according to the invention.

FIG. 1 shows an embodiment of a preparation device 1 according to the invention. The preparation device 1 comprises an elongated cuboid case 11 made of a disposable rigid plastic material. From left to right a top side of the case 11 is provided with a round sample collecting opening 112, an elongated transverse window 111 and a main see-through portion 113. Through the see-through portion 113 an interior of the case 11 is visible in which a substrate 12 is arranged.

In a side wall of the case 11 a near field communication (NFC) chip 114 is embedded such that it is integral with the case 11. In the NFC chip 114 a unique ID of the preparation device 1 is stored such that it is automatically traceable and derivable which specific preparation device 1 is processed. The NFC chip 114 is writable and is adapted to keep record of usage of the preparation device 1. In particular, a quantity value derived by means of the preparation device 1 and calibration data can be stored in the NFC chip 114.

Figure 2:
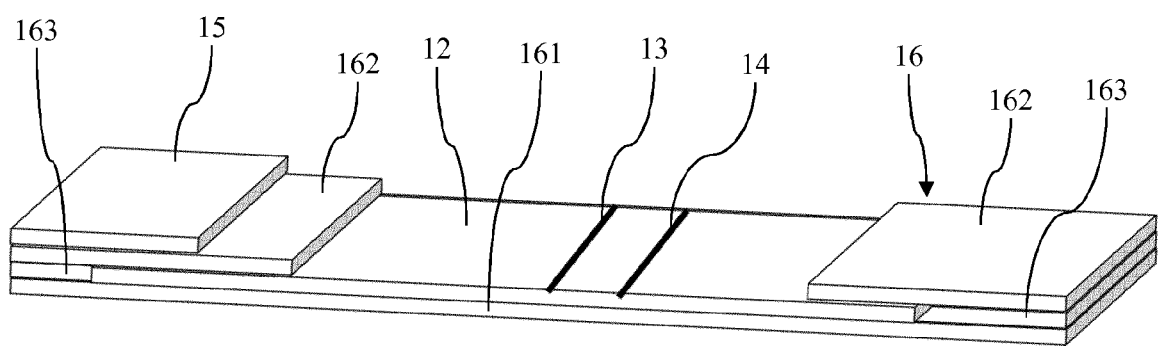
FIG. 2 shows a schematic perspective view of some interior components of the preparation device of FIG. 1.

In FIG. 2 a test strip arranged in the interior of the casing 11 is shown in more detail. Thereby, it can be seen that the test strip comprises the strip shaped substrate which is partially covered by a stabilizing structure 16. In particular, the stabilizing structure comprises a back card 161 forming the bottom of the test strip on which the substrate 12 is placed. Besides both longitudinal ends of the substrate 12 a side card 163 is arranged on the back card 161 and on top of the side cards 163 and the substrate a top card 162 is arranged. The top card 162 only partially covers the top side of the substrate 12. In particular, a section of the top side of the substrate 12 corresponding to the see-through portion 113 of the case 11 is open.

On the left-hand side a sample pad 15 is positioned on the top card 162. The sample pad 15 is located beneath the sample collecting opening 112 when the test strip is inside the case 11 such that a bodily fluid, i.e. blood, provided through the sample collecting opening 112 is received and gathered by the sample pad 15 as a reservoir. The sample pad 15 is in fluid connection with the substrate 12.

The substrate 12 is equipped with a capillary network configured to transport the blood. In particular, when a probe of blood of a patient is provided through the sample collecting opening 112 into the sample pad 15, a portion of it is forwarded to the substrate 12 and transported along the substrate 12 by and via its capillary network. The substrate 12 is provided with a predefined concentration of a fluorescent marker having an antibody capable of binding to anti-mullerian hormone (AMH) as target biomolecule. Thereby, the fluorescent marker emits a reaction light as reaction radiation when excited by a light source as excitation source. In particular, when bound to AMH and excited by the light source, the fluorescent marker emits the reaction light at an intensity proportional to a quantity of AMH in the probe of blood. In particular, the substrate 12 is embodied such that the fluorescent marker bound to AMH is visible at a concentration line 13 on the top surface of the substrate 12.

The substrate 12 is further provided with a fluorescent calibration marker comprising α-fetoprotein or Vitamin D. It is capable to validate the correct functioning of the preparation device 1 by checking on a relationship between measured values and corresponding known values derived from a standard function. In particular, the substrate 12 is embodied such that the calibration marker bound to AMH is visible at a calibration line 14 on the top surface of the substrate 12.

Figure 3:
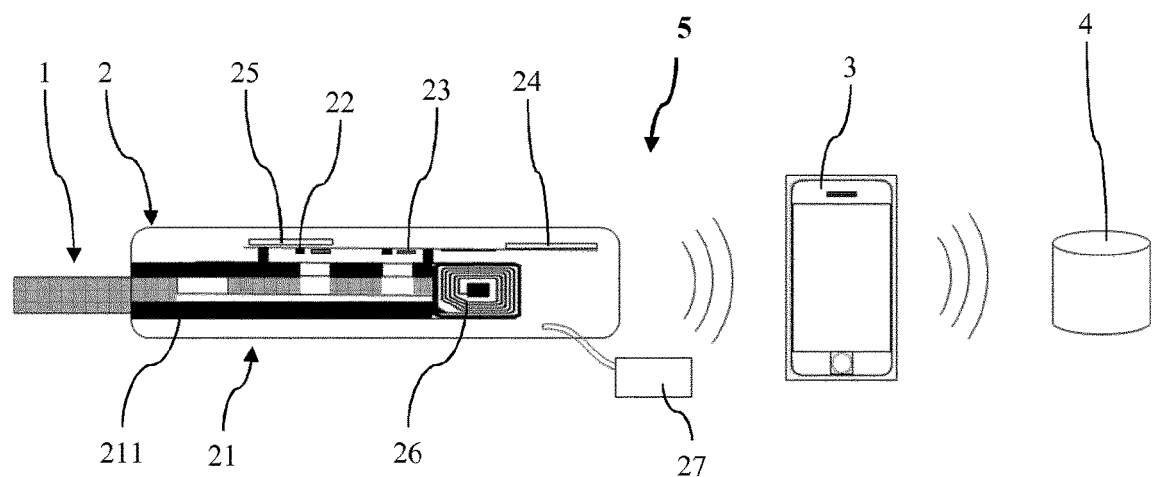
FIG. 3 shows schematic view of an embodiment of a diagnostic system comprising an embodiment of an diagnostic apparatus according to the invention having the preparation device of FIG. 1.

FIG. 3 shows an embodiment of a diagnostic system 5 comprising an embodiment of a diagnostic apparatus 2, the preparation device 1, a smartphone 3 as mobile communication device and a server 4. The diagnostic apparatus 2 has a housing 21 equipped with seat 211. The seat 211 is embodied as a laterally open slit dimensioned to guide the preparation device 1 from left to right into a predefined position and alignment inside the diagnostic apparatus 2.

The diagnostic apparatus 2 has two light sources 22 as radiation sources or excitation sources and an optical assembly with two photo sensors 23. The left one of the light sources 22 together with the left one of the photo sensors 23 are arranged adjacent to the concentration line 13 of the substrate 12. Thereby, the left-hand photo sensor 23 is arranged to receive light of the left-hand light source 22 reflected by the fluorescent marker bound to AMH at the concentration line 13. In particular, the optical assembly is adapted to measure power spectral intensity values of the reaction light emitted by a product of reaction on the preparation device 1, wherein the power spectral intensity values are proportional to a quantity of the AMH in the probe of blood.

Similarly, the right one of the light sources 22 together with the right one of the photo sensors 23 are arranged adjacent to the calibration line 14 of the substrate 12. Thereby, the right-hand photo sensor 23 is arranged to receive light of the right-hand light source 22 reflected by the calibration marker bound to AMH at the calibration line 13.

The diagnostic apparatus 2 further comprises a power supply 27 and an electronic assembly with a processor 25. The power supply 27 is arranged to deliver electric energy to all electronic components of the diagnostic apparatus 2. The processor 25 is arranged to process and convert the power spectral intensity values measured by the optical assembly to a quantity value of the AMH in the probe of blood. The electronic assembly further has a data Wireless Local Area Network (WLAN) adapter 24 and a NFC chip 26 as exchange equipment. The NFC chip 26 is adapted to receive data from the preparation device 1 via its NFC chip 114. The WLAN adapter 24 is embodied to send data to the smartphone 3. The smartphone 3 runs a dedicated software adapting the smartphone 3 to receive and display the quantity value of AMH in the probe of blood.

The smartphone 3 is further connected to the server 4, e.g., via the Internet. The server 4 is arranged to receive data signals from the smartphone 3 which data signals correspond to measured quantity values of the AMH in the probe of blood. It is further adapted to send data signals to the smartphone corresponding to an evaluation of the measured quantity value.

More specifically, the server 4 comprises a data storage and is adapted to anonymize data received from the smartphone, to store the anonymized data in the data storage, to evaluate the stored data with respect to a specific topic and to provide results of the evaluation of the stored data. The smartphone 3 receives data signals corresponding to the results of the evaluation of the stored data from the server 5. Such results can, e.g., be related to a forecast of a medical outcome for the patient.

Figure 4:
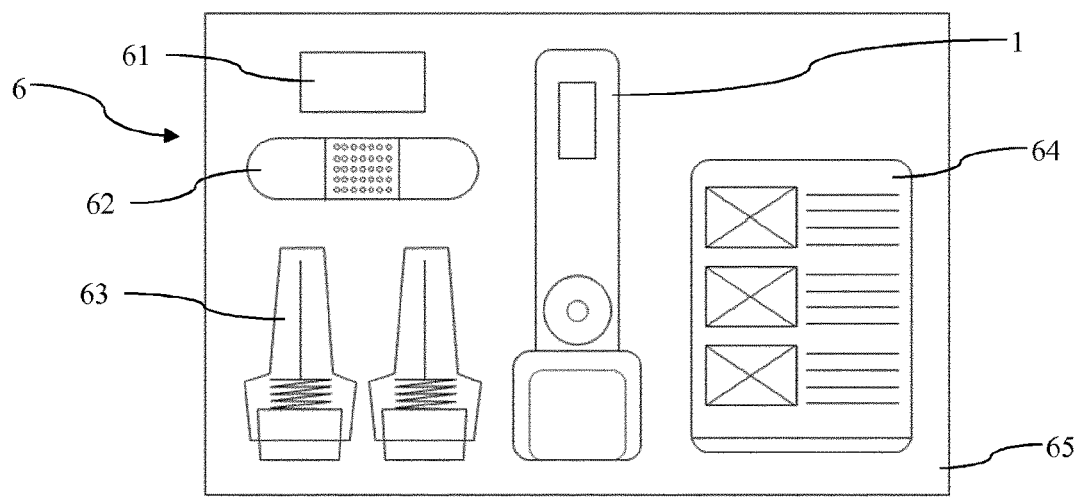
FIG. 4 shows a schematic view of an embodiment of a diagnostic kit according to the invention having the preparation device of FIG. 1.

In FIG. 4 a kit 6 is shown comprising a box 65 in which one preparation device 1, two lancets 63, a disinfection wipe 61, a plaster 62 and a instructions manual 64 are arranged. Thereby, the kit 6 provides a patient with everything required for a test cycle.

Figure 5:
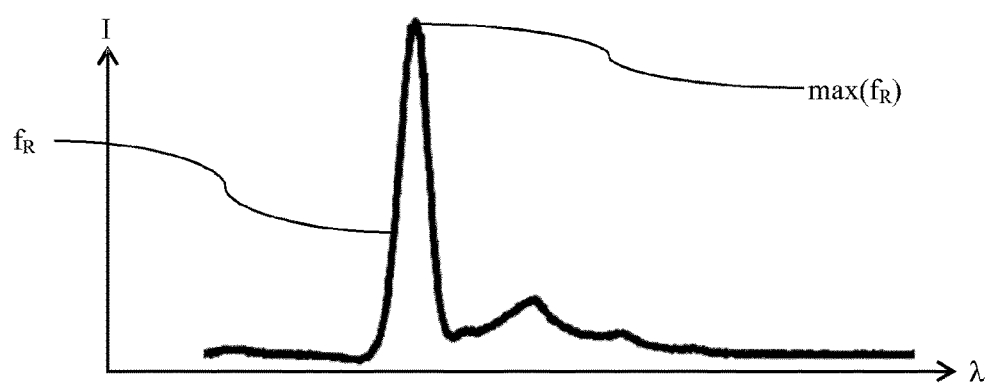
FIG. 5 shows a graph of a measured spectrum of light reflection provided within the diagnostic system of FIG. 3.

FIG. 5 shows a graph of the function of the energy spectrum of the reflected light detected by the left hand photo sensor 22. In particular, the intensity of the reflected light is displayed versus the wavelength of the light. To derive the concentration from this graph it would mathematically be required to integrate the curve. However, since the function has a clear and sharp peak the concentration can be correlated to the height of the peak which makes a very efficient evaluation of the concentration possible at an appropriate accuracy.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims.

In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below.

The disclosure also covers all further features shown in the FIGS. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. A diagnostic apparatus for the measurement of a quantity of a target biomolecule in a probe of a bodily fluid prepared by a preparation device that is configured to prepare a sample for measurement of the target biomolecule in the probe of the bodily fluid, the preparation device comprising:
   a substrate with a capillary network configured to transport the probe of the bodily fluid along the substrate,
   wherein the substrate is provided with a fluorescent, reflective or self-luminescent marker that is configured to bind with the target biomolecule to emit a reaction radiation, such that when the fluorescent, reflective or self-luminescent marker is bound to the target biomolecule together they are configured to emit the reaction radiation at an intensity proportional to the quantity of the target biomolecule in the probe of the bodily fluid, and the diagnostic apparatus comprising:
   a housing having a seat arranged to accommodate the preparation device in a predefined position and orientation;
   an excitation source adapted to illuminate the substrate of the preparation device;
   an optical assembly adapted to measure power spectral intensity values of a reaction radiation emitted by a product of reaction on the preparation device, wherein the power spectral intensity values are proportional to the quantity of the target biomolecule in the probe of the bodily fluid; and
   an electronic assembly adapted to process and convert the power spectral intensity values measured by the optical assembly to a quantity value of the target biomolecule in the probe of the bodily fluid,
   wherein the electronic assembly comprises a data exchange equipment adapted to receive data from the preparation device and to send data to a remote handheld communication device adapted to receive and display the quantity value of the target biomolecule in the probe of the bodily fluid, and
   wherein, when the preparation device is arranged in the seat of the housing, the optical assembly is arranged to ensure a first measurement alignment between the excitation source and the substrate of the preparation device illuminated by the excitation source and to ensure a second measurement alignment between the substrate of the preparation device emitting a reaction light and the electronic assembly.

2. The diagnostic apparatus of claim 1, comprising a database storage adapted to store quantity values of the target biomolecule in the probe of the bodily fluid.

3. The diagnostic apparatus of claim 1, wherein the data exchange equipment comprises a near field communication structure adapted to store a unique identifier of the diagnostic apparatus and adapted to exchange data with a near field communication arrangement of the preparation device.

4. The diagnostic apparatus of claim 1, wherein the housing includes a guide for sliding the preparation device relative to the housing into the predefined position and orientation.

5. The diagnostic apparatus of claim 1, wherein the optical assembly is arranged to subtract illumination light by the excitation source from a light reflected by the preparation device such that the reaction light emitted by the product of reaction on the substrate of the preparation device is isolated.

6. The diagnostic apparatus of claim 5, wherein the electronic assembly comprises a photo sensor adapted to measure the reaction light emitted by the product of reaction on the substrate of the preparation device, once isolated from the illumination light by the excitation source.

7. The diagnostic apparatus of claim 6, wherein the electronic assembly comprises a digital processor programmed to execute algorithms on a signal corresponding to the measured quantity value of the target biomolecule in the probe of the bodily fluid, and/or comprising an analog-to-digital converter cooperating with the photo sensor for digitalization of the measured quantity value of the target biomolecule in the probe of the bodily fluid.

8. The diagnostic apparatus of claim 1, wherein the electronic assembly comprises an energy storage device and/or a connection to an external power supply, adapted to power electronic components of the diagnostic apparatus.

9. The diagnostic apparatus of claim 1, wherein the data exchange equipment of the electronic assembly is configured to identify the remote handheld communication device of an authorized user and to send data exclusively to the authorized remote handheld communication device, and wherein the data exchange equipment of the electronic assembly is configured to identify the remote handheld communication device by providing a unique pairing identification to the remote handheld communication device and by receiving a match signal from the remote handheld communication device.

10. The diagnostic apparatus of claim 1, further comprising an imager arranged to generate image data of the quantity value of the target biomolecule in the probe of the bodily fluid, wherein the data exchange equipment of the electronic assembly is configured to send the image data to the remote handheld communication device.

11. A diagnostic system comprising:
a preparation device having
a substrate with a capillary network configured to transport the probe of the bodily fluid along the substrate,
wherein the substrate is provided with a fluorescent, reflective or self-luminescent marker that is configured to bind with the target biomolecule to emit a reaction radiation, such that when the fluorescent, reflective or self-luminescent marker is bound to the target biomolecule together they are configured to emit the reaction radiation at an intensity proportional to a quantity of the target biomolecule in the probe of the bodily fluid;
a diagnostic apparatus having
a seat arranged to accommodate the preparation device in a predefined position and orientation,
an excitation source adapted to illuminate the substrate of the preparation device,
an optical assembly adapted to measure power spectral intensity values of a reaction radiation emitted by a product of reaction on the preparation device, wherein the power spectral intensity values are proportional to a quantity of the target biomolecule in the probe of the bodily fluid, and
an electronic assembly adapted to process and convert the power spectral intensity values measured by the optical assembly to a quantity value of the target biomolecule in the probe of the bodily fluid,
wherein the electronic assembly comprises a data exchange equipment adapted to receive data from the preparation device and to send data to a remote handheld communication device adapted to receive and display the quantity value of the target biomolecule in the probe of the bodily fluid;
a server; and
a mobile communication device adapted to communicate with the diagnostic apparatus and the server, wherein the server is arranged to receive data signals from the mobile communication device corresponding to measured quantity values of the target biomolecule in probes of a bodily fluid and to send data signals to the mobile communication device corresponding to an evaluation of the measured quantity values, and
wherein the server comprises a data storage, and the server is adapted
to anonymize data received from the mobile communication device,
to store the anonymized data in the data storage,
to evaluate the stored data with respect to a specific topic, and
to provide results of the evaluation of the stored data.

12. The diagnostic system of claim 11, wherein providing the results of the evaluation of the stored data comprises sending data signals corresponding to the results of the evaluation of the stored data to the mobile communication device, and/or evaluating the stored data with respect to a specific topic preferably comprises generating a forecast of a medical outcome for a specific user.

13. The diagnostic system of claim 11, wherein the diagnostic system is arranged to be applied for pharmacovigilance or clinical trials.

* * * * *